United States Patent [19]
Hassett et al.

[11] Patent Number: 5,814,027
[45] Date of Patent: Sep. 29, 1998

[54] GUIDING INTRODUCER USED FOR MEDICAL PROCEDURES WITHIN THE RIGHT VENTRICLE ASSOCIATED WITH THE RIGHT VENTRICULAR OUTFLOW TRACK

[75] Inventors: James A. Hassett, Bloomington; John D. Ockuly, Minnetonka, both of Minn.

[73] Assignee: Daig Corporation, Minnetonka, Minn.

[21] Appl. No.: 696,337

[22] Filed: Aug. 13, 1996

Related U.S. Application Data

[63] Continuation of Ser. No. 421,763, Apr. 14, 1995, abandoned, which is a continuation-in-part of Ser. No. 146,744, Nov. 3, 1993, Pat. No. 5,427,119.

[51] Int. Cl.$^6$ ...................................................... A61B 5/00
[52] U.S. Cl. ................................. 604/286; 128/772
[58] Field of Search .................................. 604/280, 282, 604/170, 93; 128/772, 657

[56] References Cited

U.S. PATENT DOCUMENTS

| | | |
|---|---|---|
| 4,033,331 | 7/1977 | Guss et al. . |
| 4,117,836 | 10/1978 | Erikson . |
| 4,641,649 | 2/1987 | Walinsky et al. . |
| 4,882,777 | 11/1989 | Narula . |
| 4,883,058 | 11/1989 | Ruiz . |
| 4,898,591 | 2/1990 | Jang et al. . |
| 4,945,912 | 8/1990 | Langberg . |
| 5,016,640 | 5/1991 | Ruiz . |
| 5,215,540 | 6/1993 | Anderhub . |
| 5,228,442 | 7/1993 | Imran . |
| 5,231,994 | 8/1993 | Harmjanz . |
| 5,242,441 | 9/1993 | Avitall . |
| 5,295,493 | 3/1994 | Radisch, Jr. .......................... 128/772 |

FOREIGN PATENT DOCUMENTS

| | | |
|---|---|---|
| 0361314 | 4/1990 | European Pat. Off. . |
| 9402077 | 2/1994 | WIPO . |

OTHER PUBLICATIONS

Singer, I. et al. "Catheter Ablation for Arrhythmias", Clinical Manual of Electrophysiology, pp. 421–431 (1993).

Falk, R.H. et al. "Atrial Fibrillation, Mechanisms and Management", pp. 359–374 (1992).

Horowitz, L.N. "Current Management of Arrhythmias" pp. 373–378 (1991).

Gallagher, J.J. et al. "Catheter Technique for Closed Chest Ablation of the Atrioventricular Conduction System" N. Engl. J. Med., vol. 306, pp. 194–200 (1982).

(List continued on next page.)

*Primary Examiner*—Michael Buiz
*Assistant Examiner*—Kevin Truong
*Attorney, Agent, or Firm*—Scott R. Cox

[57] ABSTRACT

A process for the mapping and/or ablation of locations within the right ventricle associated with the right ventricular outflow tract for the treatment of ventricular tachycardia by use of ablation and/or mapping catheters guided by guiding introducers. Also disclosed are shapes for the guiding introducer to be used for the ablation and/or mapping of areas within the right ventricle associated with the right ventricular outflow tract for the treatment of ventricular tachycardia.

18 Claims, 2 Drawing Sheets

OTHER PUBLICATIONS

Tracy, C.M. "Radiofrequency Catheter Ablation of Ectopic Atrial Tachycardia Using Paced Activation Sequence Mapping" J. Am. Coll. Cardiol. vol. 21, pp. 210–217 (1993).

Saul, J.P. et al. "Catheter Ablation of Accessory Atrioventricular Pathways in Young Patients: Use of Long Vascular Sheaths, the Transeptal Approach and a Retrograde Left Posterior Parallel Approach" J. Amer. Coll. Card. vol. 21, No. 3, pp. 571–583 (1993).

Swartz J.F. et al. "Radiofrequency Endocardial Catheter Ablation of Accessory Atrioventricular Pathway Atrial Insertion Sites" Circulation, vol. 87, No. 2, pp. 487–499 (1993).

Morady, F. et al. "Long–Term Results of Catheter Ablation of Idiopathic Right Ventricular Tachycardia," Circulation, vol. 82, No. 6, pp. 2093–2099 (1990).

Klein, L.S. et al "Radiofrequency Catheter Ablation of Ventricular Tachycardia in Patients Without Structural Heart Disease" Circulation, vol. 85, No. 5, pp. 1666–1674 (1992).

Hartzler, G.O. "Electrode Catheter Ablation of Refractory Focal Ventricular Tachycardia" J. Amer. Coll. Card., vol. 2, No. 6, pp. 1107–1113 (1983).

Morady, F. et al. "Catheter Ablation of Ventricular Tachycardia with Intracardiac Shocks: Results in 33 Patients" Circulation, vol. 75, No. 5, pp. 1037–1049 (1987).

GUIDING INTRODUCER USED FOR MEDICAL PROCEDURES WITHIN THE RIGHT VENTRICLE ASSOCIATED WITH THE RIGHT VENTRICULAR OUTFLOW TRACK

This is a continuation of application Ser. No. 08/421,763 filed on Apr. 4, 1995, now abandoned which was a continuation-in-part of Ser. No. 146,744 filed on Nov. 3, 1993, U.S. Pat. No. 5,427,119.

BACKGROUND OF INVENTION

1. Field of Invention

This invention relates to introducers. More particularly, this invention relates to guiding introducers of specific shapes which guide ablation catheters for use specifically within the right ventricle of the human heart.

2. Prior Art

Introducers and catheters have been in use for medical procedures for many years. For example, one use of electrical catheters has been to convey an electrical stimulus to a selected location within the human body. Another use for sensing electrode catheters has been the monitoring of various forms of activity by diagnostic tests within the human body. Catheters can be used to examine, diagnose and treat while positioned at a specific location within the body which is otherwise inaccessible without more invasive procedures. Catheters may be inserted into veins or arteries near the body surface. These catheters are then guided to the specific location for examination, diagnosis or treatment by manipulating the catheter through the artery or vein of the human body.

Catheters, such as electrode catheters, are increasingly useful in remote and difficult to reach locations within the body, including specifically locations within the heart. However, the utilization of catheters is frequently limited because of the need for the precise placement of the electrodes of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the electrode of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,215,540, 5,016,640 and 4,883,058 disclose catheters for selective coronary angiography of the right coronary artery. U.S. Pat. No. 5,242,441 discloses a deflectable catheter for ablation procedures in the ventricular chamber. See also U.S. Pat. No. 4,033,031. In addition, U.S. Pat. No. 4,898,591 discloses a catheter with inner and outer layers containing braided portions. The '591 patent also discloses a number of different curvatures for intravascular catheters. Thus, catheters with a number of predetermined shapes have been disclosed for use during specific medical procedures generally associated with the heart or the vascular system. Because of precise physiology of the heart and the vascular system, catheters or introducers with precisely designed shapes for predetermined uses within the human heart and vascular system are increasingly important.

Catheter ablation of accessory pathways using a long vascular sheath by means of a transseptal and retrograde approach is discussed in Saul, J.P., et al. "Catheter Ablation of Accessory Atrioventricular Pathways in Young Patients: Use of long vascular sheaths, the transseptal approach and a retrograde left posterior parallel approach" J. Amer. Coll. Card., Vol. 21, no. 3, pps 571–583 (Mar. 1, 1993). See also Swartz, J.F. "Radiofrequency Endocardial Catheter Ablation of Accessory Atrioventricular Pathway Atrial Insertion Sites" Circulation, Vol. 87, no. 2, pps. 487–499 (Feb., 1993).

The use of ablation catheters for the treatment of a particular type of ventricular tachycardia within the right ventricle is disclosed, for example, in Morady F. et al. "Long-term Results of Catheter Ablation of Idiopathic Right Ventricular Tachycardia" Circulation, Vol. 82, No. 6, pp. 2093–2099 (1990). A catheter used for the treatment of, for example, right ventricular tachycardia is disclosed in U.S. Pat. No. 5,228,442. The treatment of ventricular tachycardia, including ventricular tachycardia associated with the high right ventricular outflow tract, with radiofrequency energy, is disclosed in Klein, L. S., et al. "Radiofrequency Catheter Ablation of Ventricular Tachycardia in Patients without Structural Heart Disease" Circulation, Vol. 85, No. 5, pp. 1666–1674 (1992). See also Hartzler, G. O. "Electrode Catheter Ablation of Refractory Focal Ventricular Tachycardia" J. Amer. Coll. Card., Vol. 2, No. 6, pp. 1107–13 (1983) and Morady, F., et al. "Catheter Ablation of Ventricular Tachycardia with Intracardiac Shocks: Results in 33 Patients" Circulation, Vol. 75, No. 5, pp. 1037–1049 (1987).

U.S. Pat. No. 4,641,649 discloses the use of high frequency energy for the treatment of tachycardia or cardiac dysrhythmia. See also U.S. Pat. No. 4,945,912 for the use of radio frequency energy for ablation of cardiac tissue. In addition, various articles have disclosed the ablation of specific locations within the heart by use of energy, in particular, radio frequency energy. See, for example, Gallagher, J. J. et al. "Catheter Technique for Closed-Chest Ablation of the Atrioventricular Conduction System" N. Engl. J. Med. Vol. 306, pp. 194–200 (1982); Horowitz, L. N. "Current Management of Arrhythmia" pp. 373–378 (1991); Falk, R. H. et al. "Atrial Fibrillation Mechanics and Management" pp. 359–374 (1992); and Singer, I. "Clinical Manual of Electrophysiology" pp. 421–431 (1993).

In addition, the use of radio frequency ablation energy for the treatment of Wolff-Parkinson-White Syndrome in the left atrium by use of a transseptal sheath is disclosed in Swartz, J. F. et al. "Radiofrequency Endocardial Catheter Ablation of Accessory Atrioventricular Pathway Atrial Insertion Sites" Circulation Vol. 87, pp. 487–499 (1993). See also Tracey, C. N. "Radio Frequency Catheter Ablation of Ectopic Atrial Tachycardia Using Paced Activation Sequence Mapping" J. Am. Coll. Cardiol., Vol. 21, pp. 910–917 (1993). See also U.S. Pat. Nos. 5,172,694, 5,222,501, and 5,242,441.

While a number of different catheters with predetermined shapes have been disclosed along with the preferred use of radiofrequency energy, there is still a need for guiding introducers for use in selected medical procedures, particularly within the right ventricle.

Accordingly, it is an object of this invention to prepare a guiding introducer for use in selected medical procedures in the right ventricle.

It is a further object of this invention to prepare a guiding introducer for use in selected electrophysiology procedures within the right ventricle of the heart.

Another object of this invention is to prepare a guiding introducer for use with an ablation catheter for selected ablation procedures within the right ventricle of the heart, in particular the right ventricular outflow tract.

These and other objects are obtained by the design of the guiding introducers disclosed in the instant invention.

SUMMARY OF INVENTION

The instant invention includes a process for the ablation or mapping of locations within the right ventricular outflow tract using an approach through the inferior vena cava comprising
(a) introducing into the right ventricle of the heart a precurved, guiding introducer, wherein said guiding introducer contains a lumen running lengthwise therethrough, a proximal and a distal end and wherein the introducer is comprised of first, second and third sections;
(b) introducing into the lumen of the guiding introducer an ablation and/or mapping catheter containing a proximal and distal end, wherein said catheter has one or more electrodes located at or near the distal end of the catheter;
(c) guiding the catheter to the right ventricular outflow tract of the heart by use of the guiding introducer; and
(d) mapping or ablating the selected location associated with the right ventricular outflow tract by use of the electrodes of the catheter.

In addition, the instant invention is a guiding introducer to be used in the right ventricle, specifically the right ventricular outflow tract, comprised of first, second and third sections.

DETAILED DESCRIPTION OF THE DRAWINGS

Figure 1:
FIG. 1 is a cutaway view of the heart showing the guiding introducer supporting a catheter which is in position in the right ventricular outflow tract.

A typical human heart includes a right ventricle, a right atrium, left ventricle and left atrium. The right atrium is in fluid communication with the superior vena cava and the inferior vena cava. The atrioventricular septum separates the atria from the ventricles. The tricuspid valve contained within the atrioventricular septum communicates the right atrium with the right ventricle. Located within the right ventricle is the right ventricular outflow tract which is located in the superior and interior aspect of the right ventricular septum. See FIG. 1. The mitral valve contained within the atrioventricular septum communicates the left atrium with the left ventricle. On the inner wall of the right atrium where it is connected with the left atrium is a recessed portion, the fossa ovalis. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electrochemical signals pass sequentially through the myocardium from the atrial to the ventricular tissue along a well defined route which includes the His-Purkinje system. Initial electric impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, patients diagnosed with Wolff-Parkinson-White syndrome (W-P-W) have an arrhythmia. The cause of this arrhythmia is thought to be the existence of an anomalous conduction pathway or pathways that connects the atria muscle tissue directly to the ventricular muscle tissue, thus by-passing the normal His-Purkinje system. These pathways are usually located in the fibrous tissue that connect the atrium and the ventricle. In recent years a technique has been developed to interrupt these anomalous conduction pathways by delivering energy into the tissue in which the pathways exist which eliminates the conduction of electrochemical impulses through the pathway. To accomplish this procedure a special catheter with ablation electrodes is positioned as close as possible to the anomalous conduction pathway. Energy is delivered to the tissue to disrupt the pathway. This same type of contact with the cardiac tissue is also necessary when mapping or other procedures are employed relating to these pathways.

Some ventricular tachycardia originate in the right ventricular outflow tract just inferior to the pulmonic value mapping activity should occur to determine the earliest ventricular activity. By applying ablation energy to the site of earliest activation, the tachycardia can be ablated.

Mere introduction of an ablation and mapping catheter into the right ventricle is not sufficient to effectively and efficiently perform these medical procedures, especially for the mapping or ablation of anomalous conduction pathways. The medical practitioner commonly monitor the introduction of the catheter and its progress through the vascular system by a fluoroscope. Such fluoroscopes can not easily identify the specific features of the heart in general and the critically important structures of the right ventricle in specific, thus making placement of the catheter difficult. This placement is especially difficult as the beating heart is in motion and the catheter will be moving within the right atrium and ventricle as blood is being pumped through the heart throughout the procedure. The structure and shape of the guiding introducer of the instant invention addresses and solves these problems.

Figure 2B:
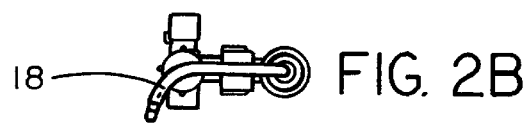
FIG. 2B is a top view of the guiding introducer rotated 90 degrees upward from the position of FIG. 2A such that the side port tubing is directed upward from the guiding introducer.
Figure 2C:
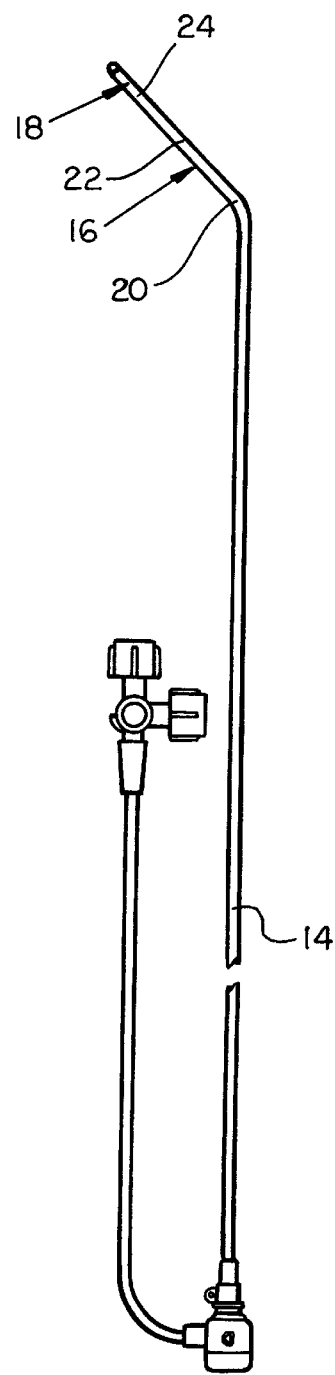
FIG. 2C is a side view of the guiding introducer rotated 90 degrees counterclockwise from the position of FIG. 2A, when viewed from the perspective of the proximal end of the guiding introducer, such that the side port tubing is directed to the left of the guiding introducer.
Figure 2A:
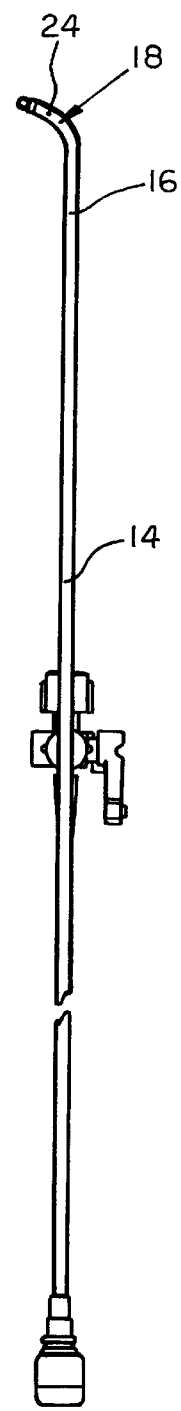
FIG. 2A is a side view of the guiding introducer for treatment of ventricular tachycardia in the right ventricular outflow tract, such that the side port tubing attached to the proximal end of the guiding introducer is located directly behind the first section of the guiding introducer.

Referring now to FIGS. 2A, 2B and 2C, the guiding introducer of the present invention for use in the right ventricle to assist in the mapping and ablation of areas of ventricular tachycardia associated with the right ventricular outflow tract which is approached through the inferior vena cava. The guiding introducer is comprised of a first, second and third section. (Each section is preferably formed as an integral portion of the entire guiding introducer without discrete divisions. However, the division of the guiding introducer into three different shaped sections better defines the overall shape of the guiding introducer.) The guiding introducer will be shown in three views. In each of the views for ease of analysis, the proximal end of the guiding introducer will be secured to a valve for attachment to a conventional side port tubing and stop cock. In each such arrangement, the shape of the guiding introducer will be described, making reference to its position in relation to the side port tubing.

In FIG. 2A, the side port is generally viewed as if it is behind the first section of the guiding introducer. The remaining figures will show the guiding introducer after rotation about the axis of one of the sections of the guiding introducer as will be described in more detail. Each will focus upon the shaped portions of the second and third sections.

The first section of the guiding introducer for use in the mapping and ablation of areas of ventricular tachycardia associated with the right ventricular outflow tract is a conventional, generally elongated, hollow, straight section of sufficient length for introduction into the patient and for manipulation from the point of insertion to the specific desired location within the heart.

The second section which is a continuation of the first section contains a curved portion and a straight portion. This curved portion curves to the left as shown in FIG. 2C at an angle of about 20 to about 70 degrees and preferably from about 30 to about 60 degrees with an arc of about 0.1 to about 0.5 in. and preferably from about 0.2 to about 0.4 in. The curved portion may be a single curve or a plurality of curves alone or in combination with one or more straight sections which achieve the same basic shape. The straight portion at the distal end of the curved portion of the second section is from about 0.8 to about 1.5 in. and preferably from about 1.1 to about 1.3 in. in length. See FIG. 2C. The first and second sections are generally coplanar (within about 20 degrees of coplanar). At the end of the straight portion of the second section is the third section, which is comprised of a simple curved portion, curving to the left as shown in FIG. 2A. This curved portion has a radius of about 0.25 to about 0.75 in. and preferably from about 0.4 to about 0.6 in. with an arc of about 60 to 120 degrees and preferably from about 80 to about 100 degrees. The curved portion may be a single curve or a plurality of curves alone or in combination with one or more straight sections which achieve the same basic shape. The curve of this third section curves out of a plane formed by the first and second sections from about 60 to about 120 degrees and preferably from about 80 to about 100 degrees. The curved portion may be a single curve or a plurality of curves alone or in combination with one or more straight sections which achieve the same basic shape. At the end of the curved portion is the distal tip of the guiding introducer.

The distal tip of the guiding introducer may be, and preferably will be, tapered to form a good transition with a dilator. This tapering is preferably less than 10 ° and more preferably about 4 ° to about 7 °. The guiding introducer preferably may also contain one or a multitude of radiopaque tip marker bands near the distal tip of the guiding introducer. The guiding introducer also preferably contains one or a plurality of vents near the distal tip of the guiding introducer, preferably three or four such vents. The vents are preferably located no more than about 1.00 in. from the tip of the guiding introducer and more preferably 0.10 to about 1.00 in. from the tip. The size of these vents should be in the range of about 40 to about $60/1000$ of an inch in diameter. These vents are generally designed to prevent air from entering the guiding introducer caused by the withdrawal of the catheter contained within the guiding introducer in the event the distal end of the guiding introducer is occluded. For example, if the tip of the guiding introducer is placed against the myocardium and the catheter located within the guiding introducer is withdrawn, a vacuum may be created within the catheter if no vents are provided. If such vacuum is formed, air may be forced back into the guiding introducer by the reintroduction of a catheter into the lumen of the guiding introducer. Such air could cause significant problems in the patient, including the possibility of a stroke, heart attack or other such problems common with air in the heart. The addition of vents near the distal tip of the guiding introducer prevents the formation of such vacuum by permitting fluid, presumably blood, to be drawn into the lumen of the guiding introducer as the catheter is being removed from the guiding introducer, thus preventing the creation of a vacuum which could cause air to enter the guiding introducer.

The guiding introducer may be made of any material suitable for use in humans which has a memory or permits distortion from, and substantial return to, the desired three dimensional or complex multiplanar shape. For the purpose of illustration and not limitation, the internal diameter of the guiding introducer may vary from about 6 to about 10 "French" (1 French equals ⅓ of a millimeter). Such guiding introducer can accept dilators from about 6 to about 10 French and appropriate guidewires. Obviously, if larger or smaller dilators or catheters are used in conjunction with the guiding introducers of the instant invention, modifications in size or shape can be made to the instant guiding introducers.

Variations in size and shape of the guiding introducer are also intended to encompass pediatric uses, although the preferred uses are for adult human hearts. It is well recognized that pediatric uses may require reductions in size of the various sections of the guiding introducer, in particular the first section, but without any significant modification to the shape or curves of the guiding introducer.

In addition, variations in size or shape of the guiding introducer are also intended to encompass the specialized situations that sometimes occur in patients with enlarged and rotated hearts.

In operation, a modified Seldinger technique is normally used for the insertion of the catheter into the appropriate vessels. For insertion of the catheter for use in the treatment of ventricular tachycardia associated with the right ventricular outflow tract, the preferred insertion site will be the right femoral vein. The appropriate vessel is accessed by needle puncture. A soft flexible tip of an appropriately sized guidewire is then inserted through and a short distance beyond the needle into the vessel. Firmly holding the guidewire in place, the needle is removed.

The guidewire is then advanced through the vessel into the inferior vena cava into the right atrium. With the guidewire in place, a dilator is then placed over the guidewire with the guiding introducer placed over the dilator. The dilator and guiding introducer generally form an assembly to be advanced together along the guidewire into the right atrium. The guidewire is then withdrawn. The dilator and guiding introducer assembly are advanced through the tricuspid valve to the right ventricle. The dilator is then withdrawn. At that point the guiding introducer will curve simultaneously interiorly and medially to pass through the tricuspid valve to the origin of the right ventricular outflow tract which is located in the superior and anterior aspect of the right ventricular septum. The catheter to be used is advanced through the lumen of the guiding introducer and is placed at an appropriate location near the right ventricular outflow tract. See FIG. 1.

By use of the guiding introducer in conjunction with fluoroscopic viewing, the distal portion of the guiding introducer can be manipulated to direct the distal end of an ablation and/or mapping catheter placed within the lumen of the guiding introducer, to a specific internal surface of the heart for the ablation and/or mapping procedure. In addition, by providing sufficient rigidity and support as the guiding introducer is held in place by the anatomical structure of the heart as well as the vasculature, the distal end of the guiding introducer can be maintained in that fixed location or surface position of the endocardial structure to permit the appropriate procedures to be performed.

If sensing procedures are involved, the guiding introducer is placed in the desired location. At that point, the electrical activity of the heart peculiar to that location can be precisely determined by use of a sensing electrophysiology catheter placed within the guiding introducer. Further, as the guiding introducer permits precise location of catheters, an ablation catheter may be placed at a precise location for destruction by the use of energy, for example, thermal, laser, direct current (low energy direct current, high energy direct current or fulgutronization procedures), or radio frequency, possible along with reduced temperature or iced procedures. This precise location of the ablation catheter electrode is important as there will be no dilution of the energy delivered due to unfocused energy being dissipated over the entire cardiac chamber and lost in the circulating blood by a constantly moving tip of the ablating catheter. This permits a significantly reduced amount of energy to be applied while still achieving efficient ablation. Further, time used to perform the procedure is significantly reduced over procedures where no guiding introducer is used.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A process for the treatment of ventricular tachycardia associated with the right ventricular outflow tract using ablation and mapping catheters comprising (a) introducing into the right ventricle a precurved, guiding introducer, wherein said guiding introducer contains a lumen running lengthwise therethrough, a proximal and a distal end, and is comprised of first, second and third sections, (b) introducing into the lumen of the guiding introducer an ablation and mapping catheter capable of ablating and mapping ventricular tissue containing a proximal and distal end, wherein said catheter has at least one electrodes located at the distal end of the catheter, (c) guiding the catheter to a selected location within the right ventricle associated with the right ventricular outflow tract by use of the guiding introducer, and (d) mapping and ablating the selected location within the right ventricle by firmly maintaining contact of the catheter against ventricular tissue associated with the right ventricular outflow tract.

2. The process of claim 1 wherein the ablating utilizes one of the following sources of ablation energy: direct current, radio frequency, microwave, ultrasound, and laser.

3. The process of claim 2 wherein the ablating is performed utilizing radio frequency energy.

4. The process of claim 1 wherein the first section is an elongated, hollow, generally straight section of sufficient length for introduction into the patient and for manipulation from the point of insertion to a desired location within the heart.

5. The process of claim 1 wherein the second section is a curved portion and a straight portion wherein the curved portion contains an overall arc, wherein the overall arc is about 20 to about 70 degrees, and wherein the straight portion is about 0.8 to about 1.5 in. in length.

6. The process of claim 5 wherein the curved portion comprises at least one curved sections.

7. The process of claim 6 wherein the curved portion also contains at least one straight sections.

8. The process of claim 1 wherein the second section is a curved portion and a straight portion, wherein the curved portion is a curve with a radius of about 0.2 to about 0.4 in. and an arc of about 30 to about 60 degrees, and wherein the straight portion is about 1.1 to about 1.3 in. in length.

9. The process of claim 1 wherein the third section is a curved portion containing an overall radius of about 0.25 to about 0.75 in. and an overall arc of about 60 to about 120 degrees ending in the distal tip of the guiding introducer wherein the third section curves out of a plane formed by the first and second sections from about 60 to about 120 degrees.

10. The process of claim 1 wherein the third section is a curve with an overall arc of about 60 to about 120 degrees ending in the distal tip of the guiding introducer, wherein said third portion curves out of a plane formed by the first and second sections from about 80 to about 100 degrees.

11. A guiding introducer for use with an ablation catheter for the ablation and mapping of areas of the right ventricle of the heart associated with the right ventricular outflow tract comprising separate and distinct first, second and third sections wherein said guiding introducer is shaped to guide the ablation catheter to the area of the heart associated with the right ventricular outflow tract.

12. The guiding introducer of claim 11 wherein the first section is an elongated, hollow, generally straight section containing proximal and distal ends wherein said first section is of sufficient length for introduction into the patient and for manipulation from the point of insertion to the desired location within the heart.

13. The guiding introducer of claim 11 wherein the second section contains a curved portion secured to the distal end of the first section followed by a straight portion, wherein the curved portion contains an overall arc, wherein the overall arc is about 20 to about 70 degrees, and wherein the straight portion is about 0.8 to about 1.5 in. in length.

14. The guiding introducer of claim 13 wherein the curved portion is comprised of at least one curved sections.

15. The guiding introducer of claim 14 wherein the curved portion also contains at least one straight sections.

16. The guiding introducer of claim 11 wherein the second section is a curved portion and a straight portion, wherein the curved portion is a curve with a radius of about 0.2 to about 0.4 in. and an arc of about 30 to about 60 degrees and wherein the straight portion is from about 1.1 to about 1.3 in. in length.

17. The guiding introducer of claim 11 wherein the third section is a curved portion with an overall arc of about 60 to about 120 degrees, ending in the distal tip of the guiding introducer, wherein the third section curves out of a plane formed by the first and second sections from about 60 to about 120 degrees.

18. The guiding introducer of claim 11 wherein the third section is a curve curving at an angle of about 60 to about 120 degrees with a radius of about 0.25 to about 0.75 in. and wherein this third section curves out of a plane formed by the first and second sections from about 80 to about 100 degrees.

* * * * *